United States Patent
Mazor et al.

(10) Patent No.: US 8,565,379 B2
(45) Date of Patent: Oct. 22, 2013

(54) COMBINING X-RAY AND VUV ANALYSIS OF THIN FILM LAYERS

(75) Inventors: Isaac Mazor, Haifa (IL); Matthew Wormington, Littleton, CO (US); Ayelet Dag, Haifa (IL); Bagrat Khachatryan, Haifa (IL)

(73) Assignee: Jordan Valley Semiconductors Ltd., Migdal Haemek (IL)

( * ) Notice: Subject to any disclaimer, the term of this patent is extended or adjusted under 35 U.S.C. 154(b) by 31 days.

(21) Appl. No.: 13/419,497

(22) Filed: Mar. 14, 2012

(65) Prior Publication Data
US 2012/0275568 A1 Nov. 1, 2012

Related U.S. Application Data

(60) Provisional application No. 61/452,163, filed on Mar. 14, 2011.

(51) Int. Cl.
G01N 23/201 (2006.01)
(52) U.S. Cl.
USPC ............................................. 378/88; 378/89
(58) Field of Classification Search
USPC ................................................... 378/86–90
See application file for complete search history.

(56) References Cited

U.S. PATENT DOCUMENTS

| | | |
|---|---|---|
| 3,091,154 A | 5/1963 | Hall |
| 3,160,752 A | 12/1964 | Bennett |
| 3,572,951 A | 3/1971 | Rothwarf et al. |
| 3,751,643 A | 8/1973 | Dill et al. |
| 3,825,347 A | 7/1974 | Kaiser |
| 4,029,419 A | 6/1977 | Schumann et al. |
| 4,040,750 A | 8/1977 | Zwiener |
| 4,368,983 A | 1/1983 | Bennett |
| 4,645,349 A | 2/1987 | Tabata |
| 4,729,657 A | 3/1988 | Cooper et al. |
| 4,837,603 A | 6/1989 | Hayashi |
| 4,899,055 A | 2/1990 | Adams |

(Continued)

FOREIGN PATENT DOCUMENTS

| | | |
|---|---|---|
| CN | 2430682 Y | 5/2001 |
| JP | H08-022129 A | 1/1996 |

(Continued)

OTHER PUBLICATIONS

Bai et al., "Group Theoretic Approach to the Enhancement of the Fourier Method for Crossed Gratings: C2 Symmetry Case", Optical Society of America, vol. 22, No. 4, pp. 654-651, Apr. 2005.

(Continued)

Primary Examiner — Hoon Song
(74) Attorney, Agent, or Firm — D. Kligler I.P. Services Ltd.

(57) ABSTRACT

Apparatus for inspection of a sample includes an X-ray source, which is configured to irradiate a location on the sample with a beam of X-rays. An X-ray detector is configured to receive the X-rays that are scattered from the sample and to output a first signal indicative of the received X-rays. A VUV source is configured to irradiate the location on the sample with a beam of VUV radiation. A VUV detector is configured to receive the VUV radiation that is reflected from the sample and to output a second signal indicative of the received VUV radiation. A processor is configured to process the first and second signals in order to measure a property of the sample.

12 Claims, 2 Drawing Sheets

(56) References Cited

U.S. PATENT DOCUMENTS

| | | |
|---|---|---|
| 4,984,894 A | 1/1991 | Kondo |
| 5,042,949 A | 8/1991 | Greenberg et al. |
| 5,045,704 A | 9/1991 | Coates |
| 5,120,966 A | 6/1992 | Kondo |
| 5,128,549 A | 7/1992 | Kaya |
| 5,164,790 A | 11/1992 | McNeil et al. |
| 5,182,618 A | 1/1993 | Heinonen |
| 5,241,366 A | 8/1993 | Bevis et al. |
| 5,251,006 A | 10/1993 | Hongis et al. |
| 5,357,448 A | 10/1994 | Stanford |
| RE34,783 E | 11/1994 | Coates |
| 5,388,909 A | 2/1995 | Johnson et al. |
| 5,432,607 A | 7/1995 | Taubenblatt |
| 5,440,141 A | 8/1995 | Horie |
| 5,452,091 A | 9/1995 | Johnson |
| 5,486,701 A | 1/1996 | Norton et al. |
| 5,493,401 A | 2/1996 | Horie et al. |
| 5,581,350 A | 12/1996 | Chen et al. |
| 5,607,800 A | 3/1997 | Ziger |
| 5,608,526 A | 3/1997 | Piwonka-Corle et al. |
| 5,686,993 A | 11/1997 | Kokubo et al. |
| 5,703,692 A | 12/1997 | McNeil et al. |
| 5,739,909 A | 4/1998 | Blayo et al. |
| 5,747,813 A | 5/1998 | Norton et al. |
| 5,754,296 A | 5/1998 | Law |
| 5,771,094 A | 6/1998 | Carter |
| 5,777,733 A | 7/1998 | Radziuk |
| 5,781,304 A | 7/1998 | Kotidis et al. |
| 5,784,167 A | 7/1998 | Ho |
| 5,798,837 A | 8/1998 | Aspnes et al. |
| 5,805,285 A | 9/1998 | Johs et al. |
| 5,835,225 A | 11/1998 | Thakur |
| 5,867,276 A | 2/1999 | McNeil et al. |
| 5,880,831 A | 3/1999 | Buermann et al. |
| 5,900,939 A | 5/1999 | Aspnes et al. |
| 5,903,351 A | 5/1999 | Jeong et al. |
| 5,917,594 A | 6/1999 | Norton |
| 5,963,329 A | 10/1999 | Conrad et al. |
| 5,991,022 A | 11/1999 | Buermann et al. |
| 6,052,401 A | 4/2000 | Wieser et al. |
| 6,091,485 A | 7/2000 | Li et al. |
| 6,122,052 A | 9/2000 | Barnes et al. |
| 6,128,085 A | 10/2000 | Buermann et al. |
| 6,129,807 A | 10/2000 | Grimbergen et al. |
| 6,181,427 B1 | 1/2001 | Yarussi et al. |
| 6,184,529 B1 | 2/2001 | Contini |
| 6,184,984 B1 | 2/2001 | Lee et al. |
| 6,222,199 B1 | 4/2001 | Freeouf |
| 6,226,086 B1 | 5/2001 | Holbrook et al. |
| 6,261,853 B1 | 7/2001 | Howell et al. |
| 6,265,033 B1 | 7/2001 | Hilliard |
| 6,275,292 B1 | 8/2001 | Thakur et al. |
| 6,278,519 B1 | 8/2001 | Rosencwaig et al. |
| 6,281,674 B1 | 8/2001 | Huang |
| 6,297,880 B1 | 10/2001 | Rosencwaig et al. |
| 6,304,326 B1 | 10/2001 | Aspnes et al. |
| 6,313,466 B1 | 11/2001 | Olsen et al. |
| 6,323,947 B1 | 11/2001 | Freeouf |
| 6,327,035 B1 | 12/2001 | Li et al. |
| 6,340,602 B1 | 1/2002 | Johnson et al. |
| 6,361,646 B1 | 3/2002 | Bibby, Jr. et al. |
| 6,392,756 B1 | 5/2002 | Li et al. |
| 6,411,385 B2 | 6/2002 | Aspnes et al. |
| 6,414,302 B1 | 7/2002 | Freeouf |
| 6,417,921 B2 | 7/2002 | Rosencwaig et al. |
| 6,433,878 B1 | 8/2002 | Niu et al. |
| 6,453,006 B1 | 9/2002 | Koppel |
| 6,483,580 B1 | 11/2002 | Xu et al. |
| 6,485,872 B1 | 11/2002 | Rosenthal et al. |
| 6,525,829 B1 | 2/2003 | Powell et al. |
| 6,538,731 B2 | 3/2003 | Niu et al. |
| 6,549,279 B2 | 4/2003 | Adams et al. |
| 6,556,303 B1 | 4/2003 | Rangarajan et al. |
| 6,556,652 B1 | 4/2003 | Mazor et al. |
| 6,572,951 B2 | 6/2003 | Hasegawa et al. |
| 6,580,510 B2 | 6/2003 | Nawracala |
| 6,590,656 B2 | 7/2003 | Xu et al. |
| 6,608,690 B2 | 8/2003 | Niu et al. |
| 6,630,673 B2 | 10/2003 | Khalil et al. |
| 6,630,996 B2 | 10/2003 | Rao et al. |
| 6,633,831 B2 | 10/2003 | Nikoonahad et al. |
| 6,639,968 B2 | 10/2003 | Yokhin et al. |
| 6,643,354 B2 | 11/2003 | Koppel et al. |
| 6,654,131 B2 | 11/2003 | Opsal et al. |
| 6,657,736 B1 | 12/2003 | Finarov et al. |
| 6,657,737 B2 | 12/2003 | Kimba et al. |
| 6,665,075 B2 | 12/2003 | Mittleman et al. |
| 6,673,637 B2 | 1/2004 | Wack et al. |
| 6,704,661 B1 | 3/2004 | Opsal et al. |
| 6,710,865 B2 | 3/2004 | Forouhi et al. |
| 6,713,753 B1 | 3/2004 | Rovira et al. |
| 6,713,775 B2 | 3/2004 | Chelvayohan et al. |
| 6,721,052 B2 | 4/2004 | Zhao et al. |
| 6,734,968 B1 | 5/2004 | Wang et al. |
| 6,765,676 B1 | 7/2004 | Buermann |
| 6,768,785 B2 | 7/2004 | Koppel |
| 6,768,967 B2 | 7/2004 | Johnson et al. |
| 6,775,015 B2 | 8/2004 | Bischoff et al. |
| 6,778,273 B2 | 8/2004 | Norton et al. |
| 6,778,911 B2 | 8/2004 | Opsal et al. |
| 6,801,309 B1 | 10/2004 | Nelson |
| 6,806,951 B2 | 10/2004 | Wack et al. |
| 6,806,971 B2 | 10/2004 | Finarov |
| 6,813,034 B2 | 11/2004 | Rosenewaig et al. |
| 6,819,426 B2 | 11/2004 | Sezginer et al. |
| 6,856,408 B2 | 2/2005 | Raymon |
| 6,879,395 B2 | 4/2005 | Oka et al. |
| 6,891,626 B2 | 5/2005 | Niu et al. |
| 6,897,456 B2 | 5/2005 | Hasegawa et al. |
| 6,897,807 B2 | 5/2005 | Kishigami et al. |
| 6,898,537 B1 | 5/2005 | McGahan |
| 6,909,507 B2 | 6/2005 | Norton et al. |
| 6,917,419 B2 | 7/2005 | Fielden et al. |
| 6,919,957 B2 | 7/2005 | Nikoonahad et al. |
| 6,934,025 B2 | 8/2005 | Opsal et al. |
| 6,979,578 B2 | 12/2005 | Venugopal |
| 6,982,792 B1 | 1/2006 | Woollam et al. |
| 6,987,832 B2 | 1/2006 | Koppel et al. |
| 7,006,235 B2 | 2/2006 | Levy et al. |
| 7,026,165 B2 | 4/2006 | DeGrandpre |
| 7,026,626 B2 | 4/2006 | Harrison |
| 7,030,999 B2 | 4/2006 | Bischoff et al. |
| 7,031,894 B2 | 4/2006 | Niu et al. |
| 7,046,375 B2 | 5/2006 | Bischoff et al. |
| 7,049,156 B2 | 5/2006 | Kueny |
| 7,053,991 B2 | 5/2006 | Sandusky |
| 7,061,614 B2 | 6/2006 | Wang et al. |
| 7,067,818 B2 | 6/2006 | Harrison |
| 7,068,363 B2 | 6/2006 | Bevis et al. |
| 7,072,050 B2 | 7/2006 | Kimba et al. |
| 7,095,511 B2 | 8/2006 | Chalmers et al. |
| 7,110,491 B2 | 9/2006 | Mazor et al. |
| 7,126,131 B2 | 10/2006 | Harrison |
| 7,130,029 B2 | 10/2006 | Wack et al. |
| 7,189,973 B2 | 3/2007 | Harrison |
| 7,196,785 B2 | 3/2007 | Nishiyama et al. |
| 7,224,471 B2 | 5/2007 | Bischoff et al. |
| 7,242,477 B2 | 7/2007 | Mieher et al. |
| 7,271,394 B2 | 9/2007 | Harrison |
| 7,282,703 B2 | 10/2007 | Walsh et al. |
| 7,342,235 B1 | 3/2008 | Harrison et al. |
| 7,349,079 B2 | 3/2008 | Zhao et al. |
| 7,359,052 B2 | 4/2008 | Fielden et al. |
| 7,391,030 B2 | 6/2008 | Harrison |
| 7,391,524 B1 | 6/2008 | Chen et al. |
| 7,394,551 B2 | 7/2008 | Harrison |
| 7,399,975 B2 | 7/2008 | Harrison |
| 7,446,876 B2 | 11/2008 | Harrison |
| 7,485,869 B2 | 2/2009 | Harrison et al. |
| 7,511,265 B2 | 3/2009 | Walsh et al. |
| 7,551,719 B2 | 6/2009 | Yokhin et al. |
| 7,579,601 B2 | 8/2009 | Harrison et al. |
| 7,622,310 B2 | 11/2009 | Harrison et al. |
| 7,643,666 B2 | 1/2010 | Setija et al. |

(56) References Cited

U.S. PATENT DOCUMENTS

| | | | |
|---|---|---|---|
| 7,663,097 | B2 | 2/2010 | Walsh et al. |
| 7,663,747 | B2 | 2/2010 | Harrison et al. |
| 7,684,037 | B2 | 3/2010 | Harrison |
| 7,804,057 | B2 | 9/2010 | Sato et al. |
| 7,804,059 | B2 | 9/2010 | Harrison |
| 7,804,934 | B2 | 9/2010 | Agnihotri et al. |
| 7,948,631 | B2 | 5/2011 | Walsh |
| 7,990,549 | B2 | 8/2011 | Walsh |
| 8,014,000 | B2 | 9/2011 | Harrison |
| 8,054,453 | B2 | 11/2011 | Harrison |
| 8,119,991 | B2 | 2/2012 | Harrison |
| 8,153,987 | B2 | 4/2012 | Hurst et al. |
| 2001/0055118 | A1 | 12/2001 | Nawracala |
| 2002/0030826 | A1 | 3/2002 | Chalmers et al. |
| 2002/0088952 | A1 | 7/2002 | Rao et al. |
| 2002/0126277 | A1 | 9/2002 | Norton et al. |
| 2002/0149774 | A1 | 10/2002 | McAninch |
| 2002/0154302 | A1 | 10/2002 | Rosencwaig et al. |
| 2002/0190207 | A1 | 12/2002 | Levy et al. |
| 2003/0071996 | A1 | 4/2003 | Wang et al. |
| 2003/0081201 | A1 | 5/2003 | Shibata et al. |
| 2003/0081725 | A1* | 5/2003 | Opsal et al. ............... 378/89 |
| 2004/0150820 | A1 | 8/2004 | Nikoonahad et al. |
| 2004/0235205 | A1* | 11/2004 | Levy et al. ............... 438/14 |
| 2005/0001172 | A1 | 1/2005 | Harrison |
| 2005/0036143 | A1 | 2/2005 | Huang |
| 2006/0001885 | A1 | 1/2006 | Hertzsch et al. |
| 2006/0066855 | A1 | 3/2006 | Boef et al. |
| 2007/0181793 | A1 | 8/2007 | Harrison |
| 2007/0215801 | A1 | 9/2007 | Walsh et al. |
| 2008/0129986 | A1 | 6/2008 | Walsh |
| 2008/0181793 | A1 | 7/2008 | Mistry et al. |
| 2008/0246951 | A1 | 10/2008 | Walsh et al. |
| 2009/0002711 | A1 | 1/2009 | Harrison |
| 2009/0248074 | A1 | 10/2009 | Kliegman et al. |
| 2010/0051822 | A1 | 3/2010 | Harrison |
| 2010/0277741 | A1 | 11/2010 | Walsh |
| 2010/0290033 | A1 | 11/2010 | Walsh |
| 2012/0170021 | A1 | 7/2012 | Walsh |
| 2012/0182542 | A1 | 7/2012 | Walsh et al. |

FOREIGN PATENT DOCUMENTS

| | | | |
|---|---|---|---|
| JP | 10160572 | A | 6/1998 |
| JP | 2000205966 | A | 7/2000 |
| JP | 2000249600 | A | 9/2000 |
| JP | 2002243381 | A | 8/2002 |
| JP | 2003202266 | A | 7/2003 |
| JP | 2003232681 | A | 8/2003 |
| WO | 9902970 | A1 | 1/1999 |
| WO | 2007126612 | A2 | 11/2007 |
| WO | 2007130295 | A2 | 11/2007 |

OTHER PUBLICATIONS

Bai et al., "Reduction of Computation Time for Crossed Gratings Problems: A Group Theoretic Approach", Optical Society of America, vol. 21, No. 10, pp. 1886-1894, Oct. 2004.

Li, L., "Use of Fourier Series in the Analysis of Discontinuous Periodic Structure", Optical Society of America, vol. 13, No. 9, pp. 1870-1876, Sep. 1996.

Granet et al., "Efficient Implementation of the Coupled Wave Method for Metallic Lamellar Gratings in TM Polarization", Optical Society of America, vol. 13, No. 5, pp. 1019-1023, May 1996.

Lalanne et al., "Highly Improved Convergence of the Coupled Wave Method for TM Polarization", Optical Society of America, vol. 13, No. 4, pp. 779-784, Apr. 1996.

Tan, E., "Enhanced R Matrix Algorithms for Multilayered Diffraction Gratings", Applied Optics, vol. 45, No. 20, pp. 4803-4809, Jul. 19, 2006.

Kaplan et al., "Characterization of Bidimensional Gratings by Spectroscopic Ellipsometry and Angle Resolved Mueller Polarimetry", Applied Optics, vol. 43, No. 6, pp. 1233-1240, Feb. 20, 2004.

Novikova et al., "Application of Mueller Polarimetry in Conical Diffraction for Critical Dimension Measurements in Microelectronics", Applied Optics, vol. 45, No. 16, pp. 3688-3697, Jun. 1, 2006.

Bao, J., "An Optical Metrology System for Lithography Process Monitoring and Control", Thesis, University of California at Berkeley, Department of Electrical Engineering and Computer Sciences, 135 pages, Spring 2003.

Coulombe et al., "Ellipsometric—Scatterometry for Sub-01um CD Measurements", SPIE, vol. 3332, pp. 282-2393, year 1998.

Opsal et al., "Fundamental Solutions for Real-Time Optical CD Metrology", SPIE, vol. 4689, pp. 163-176, year 2002.

Bischoff et al., "New Aspects of Optical Scatterometry Applied to Microtechnology", SPIE, vol. 3215, pp. 144-155, year 1997.

Minhas et al., "Towards Sub-01 um CD Measurements Using Scatterometry", SPIE, vol. 2725, pp. 729-739, year 1996.

Bischoff et al., "Single Feature Metrology by Means for Light Scatter Analysis", SPIE, vol. 3050, pp. 574-585, year 1997.

Mills et al., "Spectral Ellipsometry on Patters Wafers", SPIE, vol. 2637, pp. 194-203, year 1995.

Depine et al., "Internal Symmetries in Conical Diffraction from Metallic Gratings", Journal of Modern Optics, vol. 48, No. 8, pp. 1405-1411, year 2001.

Xie et al., "Transmission of Light Through Periodic Arrays of Sub-Wavelength Slits in Metallic Hosts", Optics Express, vol. 14, No. 14, pp. 6400-6413, Jul. 10, 2006.

Robert et al., "Control of the Homogeneity of an Optical Grating by a Neural Characterization", Optical Engineering, vol. 44, No. 3, 5 pages, Mar. 2005.

Boyer et al., "Diffraction Theory: Application of the Fast Fourier Factorization to Cylindrical Devices with Arbitrary Cross Section Lighted in Conical Mounting", Optical Society of America, vol. 23. No. 5, pp. 1146-1158, May 2006.

Cordeiro et al., "Phase Constraint for the Waves Diffracted by Lossless Symmetrical Gratings at Littrow Mount", Optical Society of America, vol. 23, No. 1, pp. 166-171, Jan. 2006.

Robert et al., "Experimental Characterization of Subwavelength Diffraction Gratings by an Inverse-Scattering Neural Method", Optical Society of America, vol. 19, No. 12, pp. 2394-2402, Dec. 2002.

Robert et al., "Characterization of Optical Diffraction Gratings by Use of a Neural Method", Optical Society of America, vol. 19, No. 1, pp. 24-32, Jan. 2002.

Li, L., "Symmetries of Cross-Polarization Diffraction Coefficients of Gratings", Optical Society of America, vol. 17, No. 5, pp. 881-887, May 2000.

Logofatu et al., "Identity of the Cross-Reflection Coefficients for Symmetric Surface-Relief Gratings", Optical Society of America, vol. 16, No. 5, pp. 1108-1114, May 1999.

Zolla et al., "Method of Fictitious Sources as Applied to the Electromagnetic Diffraction of a Plane Wave by a Grating in Conical Diffraction Mounts", Optical Society of America, vol. 13, No. 4, pp. 796-802, Apr. 1996.

Peng et al., "Efficient Implementation of Rigorous Coupled-Wave Analysis for Surface-Relief Gratings", Optical Society of America, vol. 12, No. 5, pp. 1087-1096, May 1995.

Li, L., "Multilayer Modal Method for Diffraction Gratings of Arbitrary Profile, Depth and Permittivity", Optical Society of America, vol. 10, No. 12, pp. 2581-2591, Dec. 1993.

Li et al., "Convergence of the Coupled-Wave Method for Metallic Lamellar Diffraction Gratings", Optical Society of America, vol. 10, No. 6, pp. 1184-1189, Jun. 1993.

Peng, S., "Rigorous Formulation of Scattering and Guidance by Dielectric Grating Waveguides: General Case of Oblique Incidence", Optical Society of America, vol. 6, No. 12, pp. 1869-1883, Dec. 1989.

Moharam et al., "Rigorous Coupled-Wave Analysis of Grating Diffraction-E-mode Polarization and Losses", Optical Society of America, vol. 73, No. 4, pp. 451-455, Apr. 1983.

Moharam et al., "Diffraction Analysis of Dielectric Surface-Relief Gratings", Optical Society of America, vol. 72, No. 10, pp. 1385-1392, Oct. 1982.

Moharam et al., "Rigorous Coupled-Wave Analysis of Planar-Grating Diffraction", Optical Society of America, vol. 71, No. 7, pp. 811-818, Jul. 1981.

(56) References Cited

OTHER PUBLICATIONS

Knop, K., "Rigorous Diffraction Theory for Transmission Phase Gratings with Deep Rectangular Grooves", Optical Society of America, vol. 68, No. 9, pp. 1206-1210, Sep. 1978.
Kong, J., "Second-Order Coupled-Mode Equations for Spatially Periodic Media", Optical Society of America, vol. 67, No. 6, pp. 825-829, Jun. 1977.
Azzam et al., "Generalized Ellipsometry for Surfaces with Directional Preference: Application to Diffraction Gratings", Journal of the Optical Society of America, vol. 62, No. 12, pp. 1521-1530, Dec. 1972.
Case, S., "Coupled-Wave Theory for Multiply Exposed Thick Holographic Gratings", Optical Society of America, vol. 65, No. 6,pp. 724-729, Jun. 1975.
Kaspar, F., "Diffraction by Thick, Periodically Stratified Gratings with Complex Dielectric Constant", Journal of Optical Society of America, vol. 63, No. 1, pp. 37-45, Jan. 1973.
Azzam et al., "Application of Generalized Ellipsometry to Anisotropic Crystals", Journal Optical Society of America, vol. 64, No. 2, pp. 128-133, Feb. 1974.
Burckhardt, C., "Diffraction of a Plane Wave at a Sinusoidally Stratified Dielectric Grating", Journal of Optical Society of America, vol. 56, No. 11, pp. 1502-1509, Nov. 1966.
Krukar et al., "Reactive Ion Etching Profile and Depth Characterization Using Statistical and Neural Network Analysis of Light Scattering Data", American Institute of Physics, vol. 74, No. 6, pp. 3698-3706, Sep. 15, 1993.
Li, L., "A Modal Analysis of Lamellar Diffraction Gratings in Conical Mountings", Journal of Modern Optics, vol. 40, No. 4, pp. 553-573, year 1993.
Momeni et al., "Pure Coupled Mode Analysis of Diffraction by Isotropic Transmission Volume Gratings", IEEE Transactions on Antennas and Propagation, vol. 52, No. 12, pp. 3304-3311, Dec. 2004.
Momeni et al., "Improved Coupled Wave Analysis of Two-Dimensional Planar Multiple Gratings", IEEE Transactions on Antennas and Propagation, vol. 52, No. 1, pp. 165-171, Jan. 2004.
Garnaes et al., "Profiles of a High-Aspect Radio Grating Determined by Spectroscopic Scatterometry and Atomic-Force Microscopy", Applied Optics, vol. 45, No. 14, pp. 3201-3212, May 10, 2006.
Kallioniemi et al., "Characterization of Diffraction Gratings in a Rigorous Domain with Optical Scatterometry: Hierarchical Neural-Network Model", Applied Optics, vol. 38, No. 28, pp. 5920-5930, Oct. 1, 1999.
Ahmed et al., "Comparison of Beam Propagation Method and Rigorous Coupled-Wave Analysis for Single and Multiplexed Volume Gratings", Applied Optics, vol. 35, No. 22, pp. 4426-4435, Aug. 1, 1996.
Minhas et al., "Ellipsometric Scatterometry for the Metrology of Sub-01-um-linewidth Structures", Applied Optics, vol. 37, No. 22, pp. 5112-5115, Aug. 1, 1998.
Kallioniemi et al., "Optical Scatterometry of Subwavelength Diffraction Gratings: Neural Network Approach", Applied Optics, vol. 37, No. 25, pp. 5830-5835, Sep. 1, 1998.
Huang et al., "Normal-Incidence Spectroscopic Ellipsometry for Critical Dimension Monitoring", Applied Physics Letters, vol. 78, No. 25, pp. 3893-3985, Jun. 18, 2001.
U.S. Appl. No. 12/592,773 Official Action dated Sep. 1, 2010.
Das et al., "Image Evaluation of the High-Resolution VUV Spectrometer at SURF II by Ray Tracing", Journal of Research of the National Institute of Standards and Technology, vol. 103, No. 5, pp. 483-495, Sep.-Oct. 1998.
US Reexamination Application 190 90/009,409 Official Action dated Jun. 18, 2010.
Chinese Patent Application No. 200480027513.6 Official Action dated Jul. 18, 2008.
US Reexamination Application 190 90/009,320 Official Action dated Sep. 25, 2009, and Notice of Intent to Issue Re-Exam Certificate dated Jun. 23, 2010.
Aspnes, D.E., "Determination of Optical Properties by Ellipsometry", Handbook of Optical Constants of Solids, vol. 1, pp. 104-108, Academic Press, 1998.
Bloomstein et al., "Contamination Rates of Optical Surface at 157nm in the Presence of Hydrocarbon Impurities", Optical Microlithography XV, Proceedings of the SPIE, vol. 4691, pp. 709-723, Jul. 30, 2002.
Field et al., "Method of Using the Reflectance Ratios of Difference Angles of Incidence for the Determination of Optical Constants", Applied Optics, vol. 10, No. 6, pp. 1402-1405, Jun. 1971.
Hunter, W., "Errors in Using the Reflectance vs Angle of Incidence Method for Measuring Optical Constants", Journal of the Optical Society of America, vol. 55, No. 10, part 1, pp. 1197-1204, Oct. 1965.
Hunter et al., "Thickness of Absorbing Films Necessary to Measure Their Optical Constants Using the Reflectance-Vs-Angle-of-Incidence Method", Journal of the Optical Society of America, vol. 64, No. 4, pp. 429-433, Apr. 1974.
Jellison et al., "Parameterization of the Optical Functions of Amorphous Materials in the Interband Region", Applied Physics Letter, Jul. 15, 1996 (vol. 69, No. 3, pp. 371-373), and Sep. 30, 1996 (vol. 69, No. 14, p. 2137).
Okoroanyanwu et al., "Contamination Monitoring and Control on ASML MS-VII 157nm Exposure Tool", Optical Microlithography XVII, Proceedings of the SPIE, vol. 5377, pp. 1695-1707, May 28, 2004.
International Application PCT/US2004/030859 Search Report dated Feb. 24, 2005.
Rivas, C., "Optical Characterization of Hafnium-Based High-K Dielectric Films Using Vacuum Ultraviolet Reflectometry", Proceedings of the XV International Conference on Vacuum Ultraviolet Radiation Physics, Berlin, Germany Jul. 29-Aug. 3, 2007.
International Application PCT/US2007/010003 Search Report issued Dec. 17, 2008.
U.S. Appl. No. 10/930,339 Official Action dated Sep. 29, 2009.
U.S. Appl. No. 10/930,339 Official Action dated Jan. 18, 2007.
U.S. Appl. No. 10/930,339 Official Action dated Sep. 6, 2007.
U.S. Appl. No. 10/930,339 Official Action dated Apr. 18, 2008.
U.S. Appl. No. 10/930,339 Official Action dated Nov. 13, 2008.
Moharam et al.., "Stable Implementation of the Rigorous Coupled-Wave Analysis for Surface-Relief Gratings: Enhanced Transmittance Matrix Approach", Optical Society of America, vol. 12, No. 5, pp. 1077-1086, May 1995.
Visentine, J., "Optical Characterization of Molecular Contaminant Films", Photonics Tech Briefs, Jan. 1, 2007.
U.S. Appl. No. 12/592,641 Official Action dated Aug. 20, 2010.
Japanese Patent Application # 528098/06 Official Action dated Jun. 15, 2010 (including English translation).
US Reexamination Application 190 95/000,535 Official Action dated May 14, 2010.
Acton Research Corporation, "Acton Research Purged CAMS Optical Measurement System", Acton Research Product Brochure, USA, Published prior to Sep. 23, 2003.
McPherson Inc., "Reflectometer for Sample Analysis", McPherson Product Brochure, USA, Published prior to Sep. 23, 2003.
McPherson Inc., "Spectral Reflectometer", McPherson Product Brochure, USA, Nov. 12, 2001.
McPherson Inc., "VUVaS Spectrophotometers for 115 nm to >380nm", McPherson Product Brochure, USA, published prior to Sep. 23, 2003.
McPherson Inc., "VUVaS Spectrophotometers, Made to Measure 115-380 nm", McPherson Product Brochure, USA, published prior to Sep. 23, 2003.
Rubloff, G.W., "Surface Reflectance Spectroscopy System", Technical Disclosure, ip.com, May 1, 1977.
Sopra., "SE and GXR combined on the same instrument", printed from www.sopra-sa.com on Feb. 19, 2002.
Sopra., "The Ideal Thin Film Characterization Unit for Development and Pilot Line Environment", printed from www.sopra-sa.com on Feb. 19, 2002.
Sopra., "The Thin Film Tool for Next Generation Lithography at 157 nm", printed from www.sopra-sa.com on Feb. 19, 2002.

(56) References Cited

OTHER PUBLICATIONS

Moharam et al., "Formulation for Stable and Efficient Implementation of the Rigorous Coupled-Wave Analysis of Binary Gratings", Optical Society of America, vol. 12, No. 5, pp. 1068-1076, May 1995.
Li, L. "Using Symmetries of Grating Groove Profiles to Reduce Computation Cost of the C Method", Optical Society of America, vol. 24, No. 4, pp. 1085-1096, Apr. 2007.
Sentech Instruments GMBH., "Vacuum UV Spectroscopic Ellipsometers", printed from www.sentech.de on Feb. 20, 2002.
J.A. Woolam Company, "Award Winning VUV-VASE is the latest addition to our line of Spectroscopic Ellipsometers", printed from www.jawoolam.com on Nov. 5, 2002.
Request for Ex Parte Reexamination for US Patent # 7,067,818 filed Feb. 11, 2009.
Request for Ex Parte Reexamination for US Patent # 7,067,818 filed Feb. 12, 2010.
Request for Ex Parte Reexamination for US Patent # 7,026,626 filed Nov. 7, 2008.
U.S. Appl. No. 12/590,151 Official Action dated Jun. 25, 2010.
Tan, E., "Hybrid-Matrix Algorithm for Rigorous Coupled-Wave Analysis of Multilayered Diffraction Gratings", Journal of Modern Optics, vol. 53, No. 4, pp. 417-428, Mar. 10, 2006.
Lalanne, P., "Improved Formulation of the Coupled-Wave Method for Two-Dimensional Gratings", Optical Society of America, vol. 14, No. 7, Jul. 1997, pp. 1592-1598.
Lalanne, P., "On the Effective Medium Theory of Subwavelength Periodic Structures", Journal of Modern Optics, vol. 43, No. 10, pp. 2063-2085, year 1996.
Kinber et al., "Use of Symmetry in Solving Diffraction Problems", Radio Engineering and Electronic Physics, vol. 16, pp. 581-587, year 1971.
Press et al., "Numerical Recipes in C: 15.5 Non-Linear models", The Art of Scientific Computing, Second Edition, 15.5 Non-Linear models, pp. 681-688, Cambridge University Press 2002.
U.S. Appl. No. 12/080,947 (abandoned) Official Action dated Mar. 30, 2010.
Bai et al., "Group Theoretic Approach to Enhancing the Fourier Method for Crossed Gratings with Square Symmetry", Optical Society of America, vol. 23, No. 3, pp. 572-580, Mar. 2006.
Japanese Patent Application # 2009507685 Office Action dated Apr. 3, 2012.
European Patent Application # 04784655.5 Search dated Jun. 27, 2012.
U.S. Appl. No. 12/844,851 Official Action dated Oct. 17, 2012.
U.S. Appl. No. 12/876,242 Official Action dated Nov. 19, 2010.
Hofemann, P., "From Possible to Practical—The Evolution of Nanoimprint for Patterned Media", session 6, IDEMA DISKCON Asia-Pacific conference, Singapore, Mar. 12-13, 2009.
Al-Assaad et al., "Characterizing Nanoimprint Profile Shape and Polymer Flow Behavior using Visible Light Angular Scatterometry", Journal of Vacuum Science & Technology B: Microelectronics and Nanometer Structures, vol. 25, issue 6, pp. 2396-2401, Nov. 2007.
Patrick et al., "Scatterometry for in situ measurement of pattern reflow in nanoimprinted polymers", Applied Physics Letters, vol. 93, issue 23, 233105/1-233105/3, Dec. 2008.
Bloomer, I., "Templates, DTR and BPM Media", session 7, IDEMA DISKCON Asia-Pacific conference, Singapore, Mar. 12-13, 2009.
Terry Jr, F. L., "Accuracy limitations in specular-mode optical topography extraction", Proceedings of the SPIE, vol. 5038, pp. 547-558, May 27, 2003.
U.S. Appl. No. 12/590,151 Official Action dated Mar. 17, 2011.
U.S. Appl. No. 12/834,939 Official Action dated Jun. 10, 2011.
U.S. Appl. No. 12/876,242 Official Action dated May 20, 2011.
JP Patent Application # 528098/06 Official Action dated Aug. 30, 2011.
U.S. Appl. No. 12/854,917 Official Action dated Jul. 28, 2011.
U.S. Appl. No. 12/454,837 Official Action dated Oct. 3, 2011.
U.S. Appl. No. 12/834,939 Official Action dated Oct. 29, 2010.

* cited by examiner

COMBINING X-RAY AND VUV ANALYSIS OF THIN FILM LAYERS

CROSS-REFERENCE TO RELATED APPLICATIONS

This application claims the benefit of U.S. Provisional Patent Application 61/452,163, filed Mar. 14, 2011, which is incorporated herein by reference.

FIELD OF THE INVENTION

The present invention relates generally to systems and methods for inspection and analysis, and specifically to measuring properties of thin film layers.

BACKGROUND

Various techniques for measurement of properties of thin film layers are known in the art. These techniques have become important particularly (though not exclusively) in the field of semiconductor device manufacturing, in which microcircuits are built up from thin film elements on the surface of a semiconductor wafer.

Some measurement techniques use various types of X-ray scattering. The term "scattering" is used broadly in the present patent application to refer to any and all processes by which X-ray irradiation of a sample causes X-rays to be emitted from the sample. Thus, in this context, "scattering" includes the techniques of X-ray reflectometry (XRR), X-ray diffraction (XRD), X-ray fluorescence (XRF), and small-angle (grazing-incidence) X-ray scattering (SAXS), for example. Systems and methods for thin film measurement using these various types of X-ray scattering are described, for example, in U.S. Pat. Nos. 6,639,968, 7,551,719, and 7,804,934, whose disclosures are incorporated herein by reference.

Other measurement techniques use vacuum ultraviolet (VUV) optical metrology, based typically on reflectometry and/or ellipsometry. The terms "vacuum ultraviolet" and "VUV" as used in the present patent application refer to radiation in the spectral region below 190 nm. Systems and methods for thin film metrology using VUV reflectometry are described, for example, in U.S. Pat. Nos. 7,026,626 and 7,126,131, whose disclosures are incorporated herein by reference.

SUMMARY

The capabilities of X-ray and VUV techniques are in many ways complementary: Each technique has different strengths and weaknesses in terms of the thin film parameters that it is capable of measuring, and the two techniques, when taken together, can provide a more complete, accurate picture of thin film properties. The embodiments of the present invention that are described hereinbelow provide methods and systems for combined X-ray and VUV analysis of thin films that take advantage of the synergy between the techniques.

There is therefore provided, in accordance with an embodiment of the present invention, apparatus for inspection of a sample, including an X-ray source, which is configured to irradiate a location on the sample with a beam of X-rays. An X-ray detector is configured to receive the X-rays that are scattered from the sample and to output a first signal indicative of the received X-rays. A VUV source is configured to irradiate the location on the sample with a beam of VUV radiation. A VUV detector is configured to receive the VUV radiation that is reflected from the sample and to output a second signal indicative of the received VUV radiation. A processor is configured to process the first and second signals in order to measure a property of the sample.

In one embodiment, the apparatus includes a sample chamber, which contains at least the sample and is configured to provide controlled atmospheric conditions for measurements made in the sample chamber using both the X-rays and the VUV radiation.

In another embodiment, the apparatus includes an X-ray module including the X-ray source and X-ray detector, a VUV module including the VUV source and VUV detector, and an equipment front-end module, which is configured to transfer samples between the X-ray module and the VUV module in a controlled environment.

In some embodiments, the sample includes multiple thin film layers, and the processor is configured to process the first signal in order to extract thickness parameters with respect to two or more of the layers, and to apply the thickness parameters in processing to the second signal in order to derive a composition of at least one of the layers.

Additionally or alternatively, the processor is configured to process the first signal in order to derive one or more calibration parameters, and to apply the calibration parameters in processing the second signal.

In a disclosed embodiment, the sample includes a periodic structure with an underlying residual layer, and the processor is configured to process the first signal in order to derive a thickness of the residual layer, and to apply the derived thickness is processing the second signal in order to find a dimension of the periodic structure.

There is also provided, in accordance with an embodiment of the present invention, a method for inspection of a sample, which includes irradiating a location on the sample with a beam of X-rays and generating a first signal responsively to the X-rays that are scattered from the sample. The location on the sample is irradiated with a beam of VUV radiation, generating a second signal responsively to the VUV radiation that is reflected from the sample. The first and second signals are processed in order to measure a property of the sample.

The present invention will be more fully understood from the following detailed description of the embodiments thereof, taken together with the drawings in which:

DETAILED DESCRIPTION OF EMBODIMENTS
SYSTEM DESCRIPTION

Figure 1:
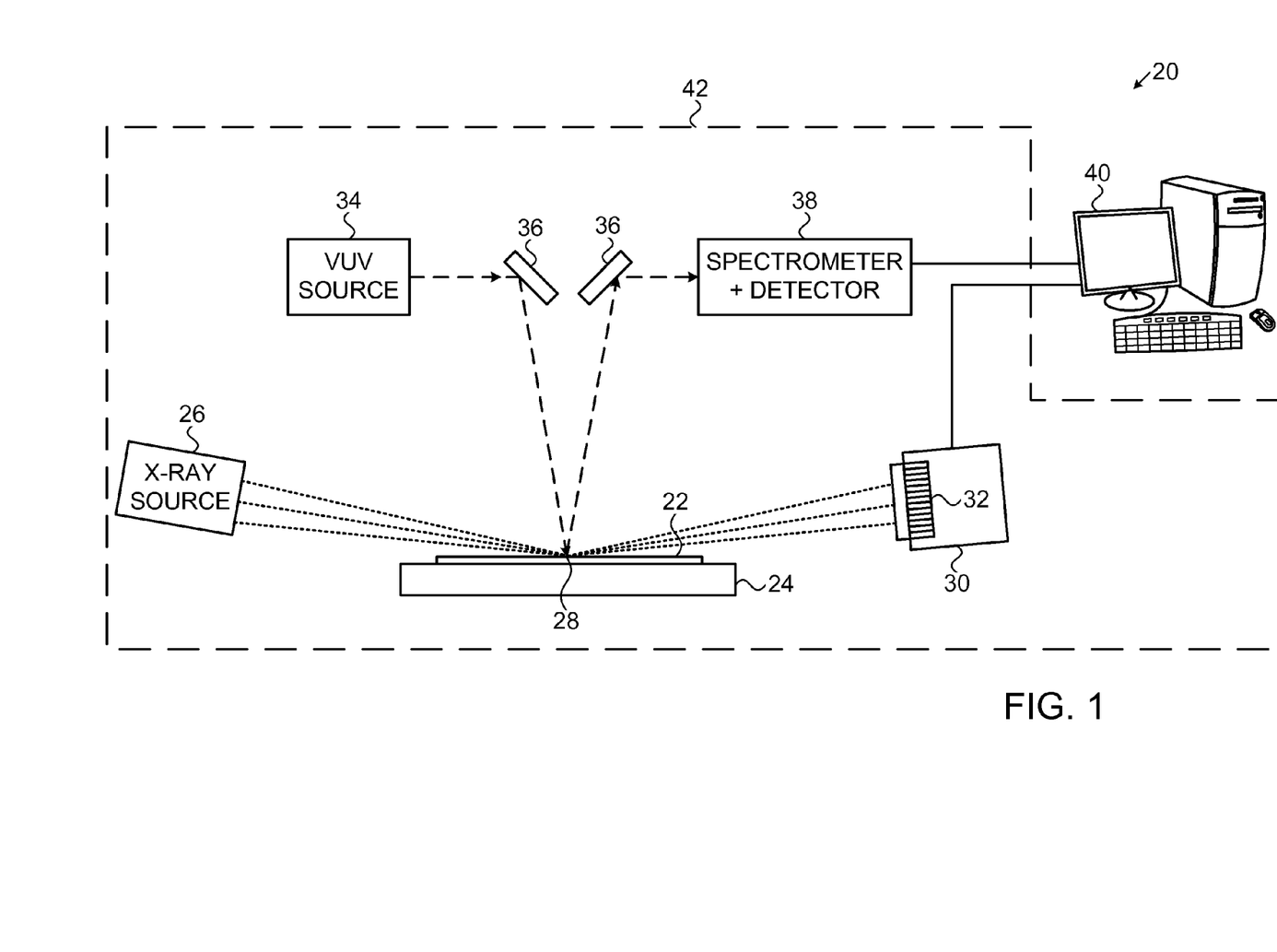
FIG. 1 is a schematic side view of a system 20 for combined X-ray and VUV analysis, in accordance with an embodiment of the present invention.

FIG. 1 is a schematic side view of a system 20 for combined X-ray and VUV analysis, in accordance with an embodiment of the present invention. System 20 in this example is configured for combined X-ray and VUV reflectometry, as will be described in greater detail hereinbelow. Alternatively, the system may be configured, mutatis mutandis, for X-ray and/or VUV measurements of other types, such as XRD, XRF, SAXS and/or VUV ellipsometry. Typically, at least some of the elements of system 20 are contained in an environmentally-controlled chamber, as described in the patents cited above, but this feature of the system is omitted from FIG. 1 for the sake of simplicity. Other system elements, such as X-ray and VUV optical components, that are not essential to an understanding of the principles of operation of system 20 are likewise omitted. These omitted system elements are described, inter alia, in the patents cited above.

An X-ray source 26 directs a converging beam of X-rays toward a measurement location 28 on the surface of a sample 22. Alternatively, optics (not shown) associated with source 26 may be configured to collimate the X-ray beam. Sample 22 in this example comprises a semiconductor wafer on which one or more thin film layers have been formed, but system 20 may similarly be used with samples of other types. Sample 22 is mounted on a motion stage 24, which permits the sample to be translated, rotated, and/or tilted to adjust the measurement location and orientation. X-rays reflected from the sample are detected by an X-ray detector 30, which typically comprises an array 32 of sensing elements, which measure the intensity of the reflected X-rays as a function of angle.

In addition, a VUV source 34 directs a beam of VUV radiation via optics 36 toward measurement location 28. The VUV source may operate either simultaneously or serially with X-ray source 26. Alternatively, in some measurement modes, either VUV source 34 or X-ray source 26 may be operated alone, independently of the other radiation source in system 20. VUV radiation reflected from sample 22 is received by a spectrometer and detector 38, which analyze the reflected radiation as a function of wavelength.

The design of system 20, as shown in FIG. 1, is advantageous in that it enables both X-ray and VUV measurements to be made, either simultaneously or serially, with sample 22 in one location. Typically, the X-ray and optical elements of system 20 are contained together with sample 22 within a sample chamber 42, which provides the appropriate, controlled atmospheric conditions for the X-ray and VUV measurements (for example, either vacuum conditions or pressurization or purge by a suitable inert gas, such as nitrogen). Alternatively, some of the X-ray and/or VUV components are coupled to the sample chamber from outside, via suitable windows. Further alternatively, X-ray and VUV measurements may be made in different chambers, as illustrated, for example, in FIG. 2 below.

A processor 40, such as a general-purpose computer with suitable interfaces and software, receives and processes the outputs of detectors 30 and 38 in order to evaluate and measure properties of the thin-film layers on sample 22. Although these processing functions are most conveniently carried out in the context of a combined X-ray/VUV system, such as system 20, some of the methods of analysis that are described below may alternatively be applied to the results of separate X-ray and VUV measurements made on the same sample in different instruments.

Figure 2:
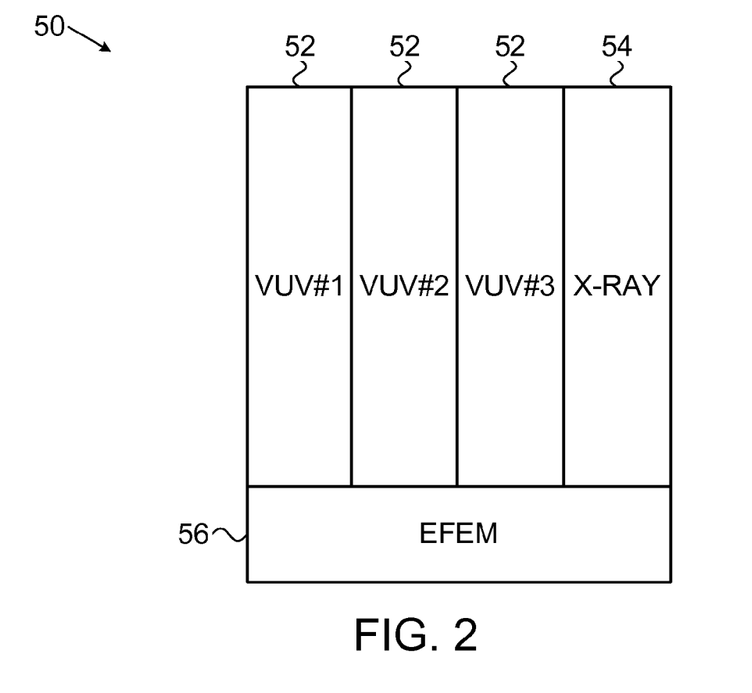
FIG. 2 is a block diagram that schematically illustrates a cluster tool, in accordance with an embodiment of the present invention.

FIG. 2 is a block diagram that schematically illustrates a cluster tool 50, which combines VUV and X-ray instruments, in accordance with an embodiment of the present invention. One or more VUV measurement modules 52 and at least one X-ray measurement module 54 share an equipment front-end module (EFEM) 56. The different measurement modules operate independently but are served by a common sample-handling system, which transfers samples between modules 52 and 54, in the controlled environment of the EFEM. This system is typically pressurized with or continuously purged by a suitable inert gas, such as nitrogen. Modules 52 and 54 in tool 50 are controlled together and coordinated by a common computer system (not shown in this figure), which may also process the measurement results.

The tool configuration shown in FIG. 2 has a number of advantages:

1) It enhances tool throughput by applying VUV measurements to multiple samples in parallel, compensating for the limited throughput of the individual VUV modules (which may be constrained by the time it takes to load each sample and then purge the measurement chamber prior to measurement).

2) It may be simpler to implement from an engineering standpoint than the combined VUV/X-ray system 20 shown in FIG. 1, while still providing many of the benefits, such as performing both XRR and VUV measurements within a short time in order to minimize contamination and oxidation of the sample surface.

3) One X-ray module can be used to calibrate samples (as explained below) for multiple VUV modules.

Measurement and Analysis Techniques

Thin-Film Thickness and Composition

As described in the patents cited above, XRR can provide accurate measurements of thin-film thickness, as well as film density and surface roughness, and can provide these measurements simultaneously for multiple layers in a thin-film stack. XRR has little chemical specificity, however, and may not be sensitive to the optical constants of the layers. XRR is also less effective in measuring very thin films (below about 10 Å) and films whose density is close to that of the substrate.

VUV reflectance, on the other hand, is sensitive to the optical constants, rather than just the density, and can be used to measure very thin films (for example, below 10 Å). Furthermore, VUV measurements have some chemical specificity because, for example, the optical absorption of certain oxides that are used in semiconductor devices, such as $SiO_2$, SiON, and $HfO_x$, increases in the VUV range. There can be correlations between the thickness and composition, however, leading to ambiguities in both parameters. In addition, when VUV measurement is applied to a multi-layer thin-film stack, it is often difficult to distinguish between the reflections from the different layers.

By using XRR to provide one (or more) physical thickness values, the ambiguities in the VUV model may be resolved. The thickness measurements of the individual layers provided by XRR can be used as a parameter in modeling the VUV reflections and thus in distinguishing the reflectance characteristics of the different layers. For example, layer parameters derived from XRR measurements can be used to create a VUV dispersion model, which can then be used in disambiguating the VUV measurement results. Thus, combining XRR and VUV measurements gives a more robust measurement of both thickness and composition of thin-film layers than can be achieved by either method alone.

VUV Dispersion Monitoring

As described in the patents cited above, VUV measurement generally requires calibration. In order to set up measurements in a VUV system, it is typically necessary to use a series of calibration samples, of known thickness and composition, for purposes of calibration as well as material dispersion modeling.

XRR may be used in combination with VUV measurement to alleviate the need for pre-measured calibration standards. Instead, XRR may be applied to an ad-hoc calibration sample or even to the sample under measurement in order to provide reliable thickness values for single thin-film layers or for multiple, stacked layers, as mentioned above. These thickness values can serve as the baseline for completing the VUV calibration process, giving a better starting point for fitting programs that are used to derive layer parameters from VUV spectral data.

Furthermore, VUV measurements are sensitive to thin oxides and airborne molecular contaminants, which tend to form on the surface of samples due to exposure to ambient air and contaminants. A single system that combines XRR and VUV measurement capabilities, such as system 20 or system 50 described above, may be useful in minimizing the time between XRR and VUV measurements, so that calibration and other combined functions are less likely to be disturbed by surface contamination and/or oxidation. Furthermore, the combination of XRR and VUV measurements can be useful in detecting and measuring the thickness of contaminant layers when such layers occur.

Measurement of Critical Dimensions

X-ray scattering techniques may be used in measuring critical dimensions of features that are formed by photolithographic processes on a semiconductor wafer surface, and particularly in measuring the width and pitch of periodic features. Measurement techniques of this sort are described, for example, in U.S. Pat. Nos. 6,556,652 and 7,110,491, whose disclosures are incorporated herein by reference.

VUV techniques may be applied in accurately measuring dimensions of periodic features below 100 nm but may suffer from correlation or crosstalk between the measured parameters. For example, VUV measurements may be subject to ambiguities with regard to the pitch and height of periodic features, such as grating-type structures of parallel lines and two-dimensional arrays of pillars, posts or holes in a film. An example of such a two-dimensional array is a bit-patterned recoding media structure, which contains a very densely-packed arrangement of small magnetic "bits." Nano-imprinting methods that are used in manufacturing such media can leave a residual layer, which tends to confuse measurements of the dimensions of such structures.

Figure 3:
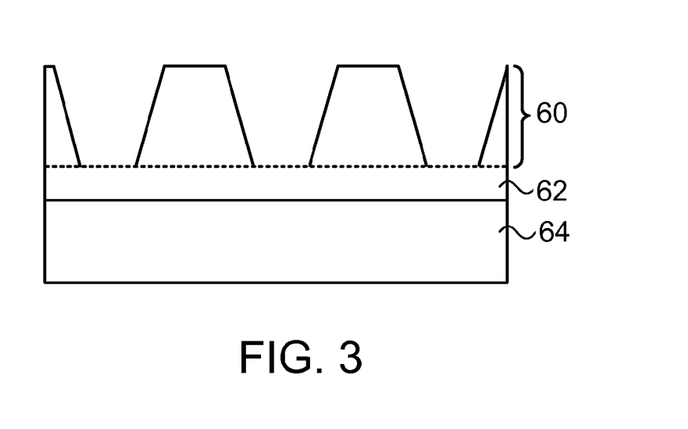
FIG. 3 is a schematic sectional view of a grating structure, whose properties are measured in accordance with an embodiment of the present invention.

FIG. 3 is a schematic sectional view of a grating structure 60, whose properties are measured using X-ray and VUV techniques in combination, in accordance with an embodiment of the present invention. Grating structure 60 in this example is formed on top of another layer 62 (such as a residual layer following etching of the grating) over a substrate 64. In this sort of situation, the VUV measurements may contain an undesired correlation between the height of grating structure 60 itself and the thickness residual layer 62 below it. XRR can be used in conjunction with VUV measurement to resolve the ambiguity by providing a reliable thickness measurement, which can then be used to constrain the VUV model and obtain a reliable measurement of dimensions, such as the pitch, of grating structure 60.

As another example, XRR can be used to provide an accurate measurement of the height of the pillars in a film. This height can then be included in a subsequent VUV analysis as a fixed parameter to remove (or at least reduce) correlations between the critical dimension (width) and sidewall angle parameters of the pillars, thereby improving the robustness of the analysis.

Alternatively, although the techniques described above use mainly combinations of XRR with VUV reflectometry, other X-ray scattering techniques, such as XRF, XRD, or SAXS, may similarly be combined with VUV.

Although the embodiments shown and described above relate to particular system configurations and certain specific types of measurements, the principles of the present invention may similarly be implemented in other X-ray and VUV measurement configurations and may be applied to measurements of other sorts of samples and thin-film parameters. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for inspection of a sample, comprising:
    an X-ray source, which is configured to irradiate a location on the sample, which includes one or more thin film layers, with a beam of X-rays;
    an X-ray detector, which is configured to receive the X-rays that are scattered from the sample and to output a first signal indicative of the received X-rays;
    a VUV source, which is configured to irradiate the location on the sample with a beam of VUV radiation;
    a VUV detector, which is configured to receive the VUV radiation that is reflected from the sample and to output a second signal indicative of the received VUV radiation; and
    a processor, which is configured to process the first signal in order to extract a thickness parameter with respect to one or more of the layers, and to apply the thickness parameter in processing to the second signal in order to derive a characteristic of at least one of the layers.

2. The apparatus according to claim 1, and comprising a sample chamber, which contains at least the sample and is configured to provide controlled atmospheric conditions for measurements made in the sample chamber using both the X-rays and the VUV radiation.

3. The apparatus according to claim 1, and comprising:
    an X-ray module comprising the X-ray source and X-ray detector;
    a VUV module comprising the VUV source and VUV detector; and
    an equipment front-end module, which is configured to transfer samples between the X-ray module and the VUV module in a controlled environment.

4. The apparatus according to claim 1, wherein the characteristic comprises a composition of the at least one of the layers.

5. The apparatus according to claim 1, wherein the processor is configured to process the first signal in order to derive one or more calibration parameters, and to apply the calibration parameters in processing the second signal.

6. The apparatus according to claim 1, wherein the the one or more thin film layers include a periodic structure with an underlying residual layer, and wherein the the thickness parameter comprises a thickness of the residual layer, and wherein the processor is configured to apply the thickness in processing the second signal in order to find a dimension of the periodic structure.

7. A method for inspection of a sample, comprising:
    irradiating a location on the sample, which includes one or more thin film layers, with a beam of X-rays;
    generating a first signal responsively to the X-rays that are scattered from the sample;
    irradiating the location on the sample with a beam of VUV radiation;
    generating a second signal responsively to the VUV radiation that is reflected from the sample;
    processing the first signal in order to extract a thickness parameter with respect to one or more of the layers; and applying the thickness parameter in processing to the second signal in order to derive a characteristic of at least one of the layers.

8. The method according to claim 7, and comprising placing the sample in a sample chamber, which is configured to provide controlled atmospheric conditions for measurements using both the X-rays and the VUV radiation, wherein irradiating the location comprises directing both the beam of the X-rays and the beam of the VUV radiation toward the location while the sample is in the sample chamber.

9. The method according to claim 7, wherein the location on the sample is irradiated with the beam of the X-rays in an X-ray module, and the location on the sample is irradiated with the beam of the VUV radiation in a VUV module, and
wherein the method comprises transferring samples between the X-ray module and the VUV module in a controlled environment performing sample handling functions in a controlled environment using an equipment front-end module that is common to the X-ray module and the VUV module.

10. The method according to claim 7, wherein the characteristic comprises a composition of the at least one of the layers.

11. The method according to claim 7, wherein processing the first and second signals comprises processing the first signal in order to derive one or more calibration parameters, and applying the calibration parameters in processing the second signal.

12. The method according to claim 7, wherein the the one or more thin film layers include a periodic structure with an underlying residual layer, and wherein the thickness parameter comprises a thickness of the residual layer, and processing the second signal comprises applying the thickness in order to find a dimension of the periodic structure.

* * * * *